United States Patent [19]

Marlon

[11] 4,432,752
[45] Feb. 21, 1984

[54] PROCEDURE FOR INTRODUCING HYPERALIMENTATION CATHETERS AND THE LIKE

[76] Inventor: Anthony M. Marlon, 888 S. Rancho Dr., Las Vegas, Nev. 89106

[21] Appl. No.: 357,835

[22] Filed: Mar. 12, 1982

[51] Int. Cl.³ ............................................. A61M 5/00
[52] U.S. Cl. ..................................... 604/53; 604/164
[58] Field of Search ............................. 604/28, 51–53, 604/158–180, 264, 280, 283

[56] References Cited

U.S. PATENT DOCUMENTS

| | | | |
|---|---|---|---|
| 4,166,469 | 9/1979 | Littleford | 604/164 X |
| 4,299,228 | 11/1981 | Peters | 604/53 X |
| 4,306,562 | 12/1981 | Osborne | 604/164 X |
| 4,327,722 | 5/1982 | Groshong et al. | 604/53 |

OTHER PUBLICATIONS

Geoghegan et al.–Nutritional Support Services–vol. 2, No. 2, Feb. 1982.

Primary Examiner—Dalton L. Truluck
Attorney, Agent, or Firm—Woodard, Weikart, Emhardt & Naughton

[57] ABSTRACT

A method for the insertion of an indwelling catheter into the subclavian vein of a patient is described herein, which includes making a first incision in the subclavian area and a second incision at a location between the sternum and the nipple. A hollow catheter having a tapered distal end is inserted into the second incision and subcutaneously tunneled to and through the first incision. A second hollow catheter, preferably a pacemaker lead introducer with a tear away sheath, is inserted through the first incision and into the subclavian vein. The indwelling catheter is passed through the hollow catheter and the tear away sheath and into the subclavian vein down to a location in the right atrium. The tear away sheath and the hollow catheter are thereafter removed and the first incision in the subclavian area is closed. A cap on the indwelling catheter exiting from the second incision is utilized to provide access to the catheter and therefore the vascular system.

23 Claims, 3 Drawing Figures

PROCEDURE FOR INTRODUCING HYPERALIMENTATION CATHETERS AND THE LIKE

BACKGROUND OF THE INVENTION

1. Field of the Invention

The present invention relates to the field of methods for the insertion of catheters into the vascular system, and more particularly to the introduction of hyperalimentation feeding catheters and the like into the subclavian vein.

2. Description of the Prior Art

In certain instances it is desirable to have repeated and frequent access to a patient's circulation for the delivery of materials such as oncology chemicals or hyperalimentation fluids. A procedure has been developed in the prior art to avoid the need for repeated venipuncture under such circumstances. This has been accomplished by the use of Hickman or Broviac type indwelling catheters.

Prior to use of the Hickman type indwelling catheter, many patients required arteriovenous shunts that have inherent problems of clotting and infection when used for infusing blood products and antibiotics. It has also been found that it is difficult to maintain nutritional status with the internal shunt, and the infusion of 50 percent dextrose in water is difficult because the blood flow through the shunt is not swift enough to handle such a viscous solution.

The Hickman indwelling right atrial catheter provides ready access to the patient's circulation both for drawing blood and for administering drugs, blood products, and total parenteral nutrition. The catheter can also be used to monitor central venous pressure and to withdraw blood for plasmapheresis. The use of this catheter can also provide added comfort and nutrition to inpatients, and outpatients can be sent home with the catheter in place to allow them the independence of administering their own parenteral nutrition.

The Hickman catheter is a modification of the Broviac catheter which also has been commonly used for total parenteral nutrition. The Hickman catheter has a larger bore with a 1.6 mm inside diameter, compared to the 1.0 mm bore of the Broviac catheter. The Hickman catheter is typically made of polymeric silicone rubber and has one or two Dacron felt cuffs used to anchor it in place subcutaneously. The external end of the catheter is threaded and comes with a male Luer lock cap. An alternate cap which is threaded and has a port through which injections can be adminstered directly may also be used, allowing less chance of contamination and air embolism.

The procedure for the placement of a Hickman catheter is generally as follows. A two inch incision is made in the deltopectoral groove below the acromion of the right clavicle, and the cephalic vein is isolated. A subcutaneous tunnel is formed using long forceps, exiting at an area between the sternum and the nipple. The catheter is pulled through the tunnel, inserted in the cephalic vein, and positioned in the lower right atrium at the entrance to the right atrium. The Dacron cuff is positioned in the subcutaneous tunnel, and the tunnel and the cuff serve as barriers to infection. This method is known in the art, and is further discussed in an article entitled "The Hickman Indwelling Catheter", by Joan Byeletich and R. O. Hickman, American Journal of Nursing, January 1980, pp. 62-65. The method of the present invention is similar, but provides a less traumatic procedure for the insertion of such a catheter.

The method of the present invention utilizes certain devices and materials, some of which are known in the art for use in other procedures. Tunneling devices in the prior art have encompassed a variety of instruments, such as the use of long forceps as previously discussed. Such devices are disadvantageous to the extent that the blunt instruments require a fair amount of disection and blunt trauma to establish the appropriate tunnel between the entrance and exit sites. Catheters for insertion into the vascular system are also well known and do not in themselves form a part of the present invention. For example, the present method may preferably use a permanent pacemaker lead introducer to accomplish the subclavian puncture.

In U.S. Pat. No. 3,946,741, issued to Adair on Mar. 30, 1976, there is described a urethral catheter and body drainage device comprising a telescoping tube assembly. The Adair patent is directed primarily to constructions for sealing the device to prevent leakage from between the tubes, and does not relate to a vascular catheter. A bladder drainage catheter and apparatus is described in U.S. Pat. No. 3,680,562, issued to Wittes et al. on Aug. 1, 1972. The Wittes et al. device includes bifurcated wings to anchor the apparatus to the skin, and also has a removeable piercing element with beveled point which extends beyond the plastic tube for insertion purposes.

A catheter holding device which can be used with the subclavian vein is disclosed in U.S. Pat. No. 4,149,535, issued to Volder on Apr. 17, 1979. The Volder device provides for the measurement of central venous pressure, and includes a side port to accept catheters for other purposes such as transfusion of liquids into the blood vessel. A hollow needle for positioning a catheter in a patient is described in U.S. Pat. No. 3,677,243, issued to Nerz on July 18, 1972. The Nerz needle includes a score line to permit the needle to be torn away for removal from a catheter inserted through it. A catheter having a particular chemical composition is disclosed in U.S. Pat. No. 4,146,033, issued to Ide et al. on Mar. 27, 1979.

SUMMARY OF THE INVENTION

Briefly described in one aspect of the present invention there is provided a method for inserting an indwelling catheter into the subclavian vein, the method comprising making a first incision in the subclavian area of the patient and a second incision at a displaced location, making a subcutaneous tunnel from the second incision to the first incision by inserting a hollow catheter therebetween, moving the indwelling catheter through the hollow catheter from the second incision to the first incision, inserting the indwelling catheter in through the first incision and into the subclavian vein, and closing the first incision to have the indwelling catheter exit from the patient only at the second incision.

It is an object of the present invention to provide a suitable method for insertion of an indwelling catheter into the subclavian vein of a patient.

Another object of the present invention is to provide a method for inserting an indwelling catheter which is readily performed and which provides a minimum of trauma to the patient.

It is a further object of the present invention to provide a method for inserting an indwelling catheter which yields an indwelling catheter having a minimum risk of infection, while providing ready access for the insertion of chemicals or nutrients to the blood system.

Further objects and advantages of the present invention will become apparent from the description of the preferred embodiment which follows.

DESCRIPTION OF THE PREFERRED EMBODIMENT

Figure 1:
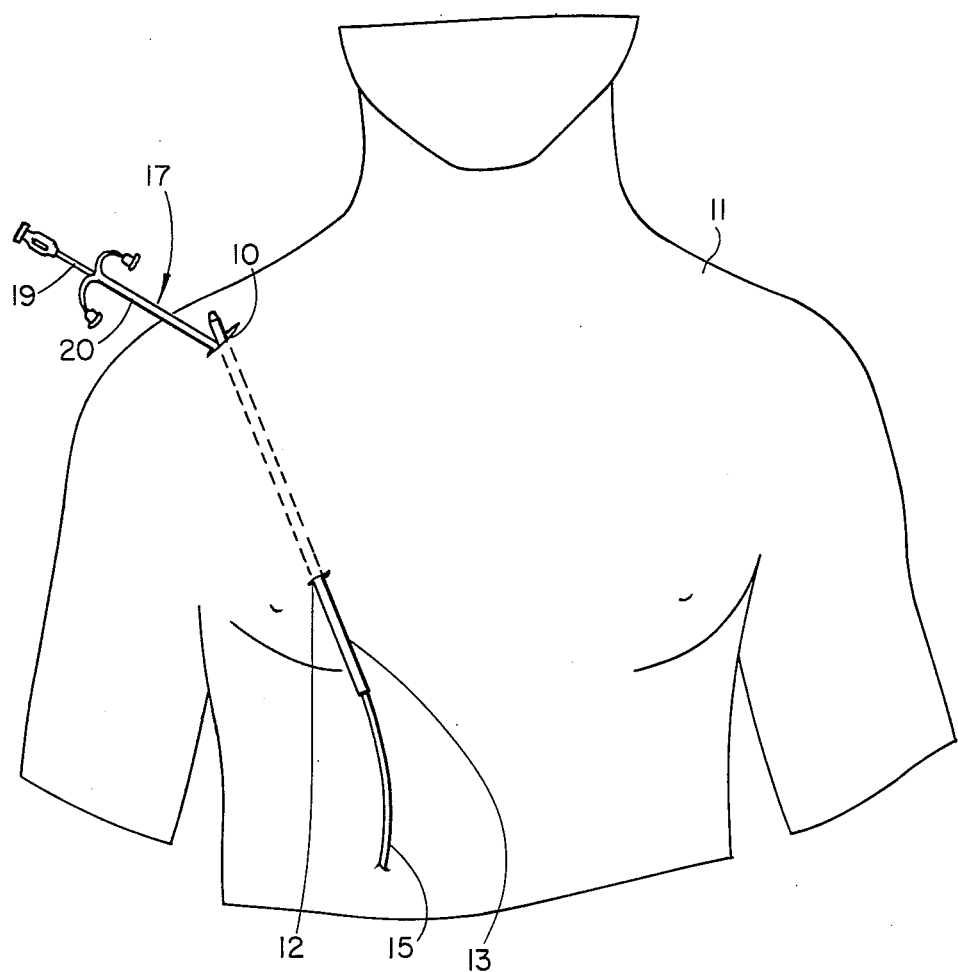
FIG. 1 is a diagramatic view of a patient showing the location of the incisions and the placement of the hollow catheter and pacemaker lead introducer inserted through the respective incisions in accordance with the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated method, and such further applications of the principles of the invention as illustrated therein being contemplated as would normally occur to one skilled in the art to which the invention relates.

The present invention relates to a method for the insertion of an indwelling catheter into the subclavian vein. In accordance with this method, and as known in the prior art, it is a purpose that the exit site for the indwelling catheter be displaced from the vein, and more generally from the vascular system. By being so displaced, and also by other means, the potential site of infection at the exit site of the catheter is sufficiently distant from the vascular system that the potential for the infection traveling to the vascular system is greatly inhibited. It is not uncommon for the catheter exit site to become a bit inflamed, and without this six to eight inch distance for the inflammation to travel, the vascular system could quickly become infected. As is also understood, the use of the subcutaneous tunnel limits the movement of the infection, as does the placement of a cuff on the indwelling catheter, as is generally known in the art.

In general terms, the procedure of the present invention is performed using the normal, sterile techniques as are applicable in the preparation of materials and instruments and in performing of the procedure. Many of the materials are commercially available, and therefore are not considered to require elaborate detail in the present description. Also, the materials used in the procedure may comprise any of the various materials well known in the art as being suitable for surgical techniques, particularly having the usual requirements such as biocompatibility. Since the materials used for the same or similar instruments as used in the present method are well known, these materials are not discussed in detail herein.

As a specific example, the indwelling catheter used in the present invention may comprise the type previously referred to as a Broviac or Hickman catheter. These catheters are commercially available under these designations from various sources, including Evermed of Medina, Wash. 98039. Also, these catheters and general methods for their use are known in the art and are described in various journal articles including the article entitled "The Hickman Indwelling Catheter" by Joan Byeletich and R. O. Hickman, *American Journal of Nursing*, January, 1980, pp. 62–65, and the pertinent portions therein are hereby incorporated by reference.

The Broviac or Hickman catheters are available in a variety of suitable sizes and materials, and in particular may be obtained as radiopaque materials and including one or two external cuffs located thereon. In addition, the indwelling catheter typically utilizes a cap to facilitate access to the catheter after it is in place. Such catheters are commercially available with a Luer lock cap or with alternate caps to provide a closure of the catheter and to facilitate access thereto.

Also, the methods for use of the indwelling catheter are well known in the art and are described in various journal articles including "The Hickman Indwelling Catheter" article previously cited and incorporated. This article discusses the procedures for using the indwelling catheter for the provision of chemicals and nutrition therethrough, or for the drawing of blood. Also described therein are particular methods used for the treatment of the incisions, and for the removal of the catheter when desired.

The procedure of the present invention may be performed either on an in-patient or an out-patient basis. The procedure is very rapidly performed with a minimum of trauma to the patient, thus permitting the procedure to be made even on an out-patient basis. Prior to performing the procedure, normal precautions and investigations suitable prior to surgical techniques should be taken. For example, the CBC and platelet count should be known prior to performing the procedure. Other normal preliminary steps are desirable as in any instance of surgery.

Referring to the drawings, the preferred embodiment for the procedure of the present invention is illustrated. In usual fashion, the chest and shoulder are prepared and draped. A subcutaneous path is made at and between the locations of the first and second incisions to be described. A small, first incision 10, preferably about one half inch long, is made in the subclavian area of the patient 11. A second incision 12, also preferably about one half inch in length, is made in the patient at a location displaced from the first incision 10. The second incision is preferably made at a location between the sternum and the nipple, thus being located about six to eight inches from the first incision.

Figure 3:
FIG. 3 is a plan view of a hollow catheter useful in accordance with the present invention for tunneling between the first and second incisions.

A subcutaneous tunnel is then made from the second incision to the first incision by use of a hollow catheter inserted into the second incision and then moved subcutaneously to and through the first incision. This hollow catheter 13 (FIG. 3) preferably includes a tapered distal end 14 which facilitates the tunneling with the catheter. The catheter preferably has a length of about 34.5 cm with an external diameter of 5.75 mm, an internal diameter of 4.0 mm and a bevel or taper of 12 mm.

The indwelling catheter 15 is inserted through the hollow catheter from the second incision to and through the first incision. It will be appreciated that the indwelling catheter 15 may be inserted into the hollow catheter 13 either prior to or after the tunneling is accomplished. In a preferred method, the indwelling catheter 15 is inserted into the hollow catheter 13 and the hollow catheter is thereafter tunneled from the second incision to and through the first incision.

When the indwelling catheter has been suitably positioned in the tunnel, the hollow catheter 13 may be removed. The removal of the hollow catheter 13 may be accomplished preferably when the indwelling catheter is in its final position as will be described further. The indwelling catheter is also inserted into the subclavian vein and positioned as desired relative the right atrium, and the hollow catheter 13 may desirably be removed after this placement of the indwelling catheter is achieved.

Figure 2:
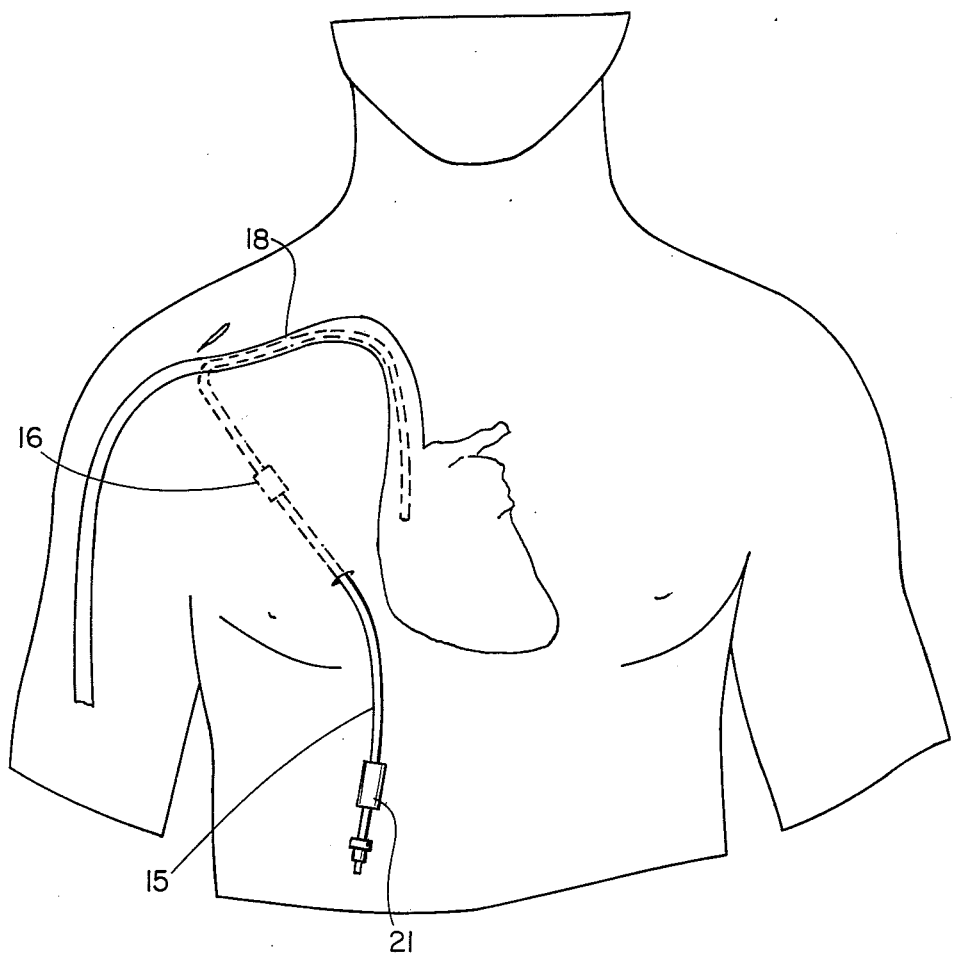
FIG. 2 is a diagramatic view showing the location of the indwelling catheter relative the patient.

The indwelling catheter 15 may preferably include a cuff 16 (FIG. 2). The ultimate location of the indwelling catheter 15 will then preferably have the cuff 16 located in the tunnel formed the hollow catheter 13. In this fashion, the cuff will aid in fixing the indwelling catheter in place, and also acts as an infection barrier. Both of these purposes are accomplished due, at least in part, to the fact that the surrounding tissue will grow into the cuff and hold the cuff in place and also form the infection barrier.

Entry in a percutaneous manner is made into the subclavian vein through the first incision 10. The purpose of this entry is to insert the indwelling catheter in through the first incision and into the subclavian vein for its final placement in the vascular system. Most preferably, this is accomplished by inserting a second hollow catheter through the first incision and into the subclavian vein, with the indwelling catheter thereafter being inserted through this second hollow catheter followed by removal of the second hollow catheter. Most desirably, the second hollow catheter has a tear away sheath for removal from the indwelling catheter.

In the most preferred method, an 11 French pacemaker introducer set with a tear away sheath is used as the second hollow catheter. These catheters are available from a variety of sources, and this method has been successfully performed utilizing a tear away sheath catheter available from Cook, Incorporated of Bloomington, Ind. 47401. Such catheters are described in U.S. Pat. No. 4,306,562, issued to Osborne on Dec. 22, 1981 and assigned to Cook, Incorporated, and the pertinent portions of such patent are hereby incorporated by reference.

In this preferred embodiment, the pacemaker introducer 17 is inserted through the first incision 10 and into the suclavian vein 18 (FIG. 2) in accordance with known technique, such as described in the U.S. Pat. No. 4,306,562, incorporated herein. A simple technique for the insertion of a pacemaker lead introducer may be briefly described as follows. The introducer includes an internal needle 19 and an external, tear away sheath 20. The needle is used to enter the subclavian vein and the sheath is thereafter extended down the needle and into the vein. The internal needle 19 is then removed, leaving only the external sheath 20 which extends into the subclavian vein and has a hollow core for reception of the indwelling catheter 15.

In accordance with the present method, it is preferable to make the entry into the subclavian vein with the introducer 17 prior to performing the tunneling with the hollow catheter 13, although either step could be performed first. With the preferred method, the tunneling is accomplished second and the indwelling catheter is then quickly drawn through the hollow catheter 13 and inserted into the tear away sheath 20 to the proper location within the subclavian vein. The sheath 20 is then torn apart into separable, longitudinal halves which are readily removed from the indwelling catheter. The indwelling catheter can then be adjusted in the proper location and positioned so that it does not extend out of the patient at the site of the first incision 10. This may be accomplished, for example, by drawing the indwelling catheter in the direction outward of the second incision. This step may be accomplished either before or after the hollow catheter 13 has been removed, but of course would require that the hollow catheter when present be withdrawn to a point so that it too does not extend outside of the first incision.

In locating the indwelling catheter in the proper position, customary techniques may be used. The catheter is preferably measured to have its tip in the area of the right atrium and the catheter is then cut to the desired length. The catheter is inserted into the sheath, using fluoroscopy, down to the right atrium and the sheath is then removed.

Once the above steps have been accomplished, the first incision 10 is closed with subcuticular suture and dressings are put in place at the incision and at the exit site 12. The catheter is then flushed with heparinized saline, having 0.3 cc to 1,000 U/cc heparin and 30 cc normal saline. The proximal end portion of the indwelling catheter 15 is removed and a suitable cap 21 is put in place. A variety of caps 21 may suitably be used and are commercially available, such as those discussed with respect to the Broviac and Hickman catheters.

In accordance with the described method, a simple procedure is provided for insertion of an indwelling catheter into the subclavian vein with a minimum of trauma to the patient. The indwelling catheter is then useful for the variety of purposes previously discussed and known in the art. The end of the catheter remains exposed through the second incision 12, and desirably has a cap, such as a stopcock arrangement, to allow and facilitate access to the tube for use in the various described manners. The use of the tunneling, particularly in the non-traumatic way provided herein, provides a substantial inhibition to passage of infection from the second incision to the vascular system.

When desired, the indwelling catheter can be readily removed by the usual technique. For example, the exit site may be cleansed with hydrogen peroxide and the catheter then firmly grasped and pulled steadily with constant pressure until the fibrous tissue around the cuff loosens and the line slides free. If the cuff remains attached to the tissue, this should not be of concern unless there is an infection at that point. Surgical removal of the catheter may be necessary if the catheter is difficult to remove or if it breaks in this process.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for the insertion of an indwelling catheter into the subclavian vein of a patient which comprises the steps of:

a. making a first incision in the subclavian area of the patient;

b. making a second incision in the patient at a location displaced from the first incision;

c. making subcutaneous tunnel from the second incision to the first incision, said making of the tunnel comprising moving a hollow catheter into the second incision and subcutaneously to and through the first incision;

d. moving the indwelling catheter through the hollow catheter from the second incision to and through the first incision;

e. after step d., removing the hollow catheter from the subcutaneous tunnel;

f. inserting the indwelling catheter in through the first incision and into the subclavian vein; and g. closing the first incision to have the indwelling catheter exit from the patient only at the second incision.

2. The method of claim 1 in which the hollow catheter used in step c. is a straight, cylindrical catheter having a tapered distal end.

3. The method of claim 2 in which step d. comprises inserting the indwelling catheter into the hollow catheter prior to step c., the masking of the subcutaneous tunnel with the hollow catheter thereby also moving the indwelling catheter from the second incision to and through the first incision.

4. The method of claim 1 in which the indwelling catheter includes an external cuff and step d. comprises moving the indwelling catheter to a position having the cuff located within the subcutaneous tunnel.

5. The method of claim 1 in which step b. comprises making the second incision in an area of the patient between the sternum and the nipple.

6. The method of claim 5 in which the indwelling catheter includes an external cuff and step d. comprises moving the indwelling catheter to a position having the cuff located within the subcutaneous tunnel.

7. The method of claim 5 in which the hollow catheter used in step c. is a straight, cylindrical catheter having a tapered distal end.

8. The method of claim 7 in which step d. comprises inserting the indwelling catheter into the hollow catheter prior to step c., the making of the subcutaneous tunnel with the hollow catheter thereby also moving the indwelling catheter from the second incision to and through the first incision.

9. The method of claim 8 in which the indwelling catheter includes an external cuff and step d. comprises moving the indwelling catheter to a position having the cuff located within the subcutaneous tunnel.

10. The method of claim 1 in which step f. comprises the substeps of inserting a second hollow catheter through the first incision and into the subclavian vein, thereafter inserting the indwelling catheter through the second hollow catheter and into the subclavian vein, and removing the second hollow catheter from the first incision and from the indwelling catheter.

11. The method of claim 10 in which the step of inserting a second hollow catheter into the subclavian vein is performed prior to step c.

12. The method of claim 10 in which the hollow catheter used in step c. is a straight, cylindrical catheter having a tapered distal end.

13. The method of claim 10 in which step b. comprises making the second incision in an area of the patient between the sternum and the nipple.

14. The method of claim 13 in which the hollow catheter used in step c. is a straight, cylindrical catheter having a tapered distal end.

15. The method of claim 14 in which the indwelling catheter includes an external cuff and step d. comprises moving the indwelling catheter to a position having the cuff located within the subcutaneous tunnel.

16. The method of claim 15 in which step d. comprises inserting the indwelling catheter into the hollow catheter prior to step c., the making of the subcutaneous tunnel with the hollow catheter thereby also moving the indwelling catheter from the second incision to and through the first incision.

17. The method of claim 10 in which the second hollow catheter comprises a tear away sheath and the removal of the second hollow catheter comprises tearing the sheath apart into two separable sections.

18. The method of claim 17 in which the second hollow catheter comprises a pacemaker lead introducer with a tear away sheath.

19. The method of claim 18 in which the hollow catheter used in step c. is a straight, cylindrical catheter having a tapered distal end.

20. The method of claim 1 in which step b. comprises making the second incision in an area of the patient between the sternum and the nipple.

21. The method of claim 1 in which the indwelling catheter includes an external cuff and step d. comprises moving the indwelling catheter to a position having the cuff located within the subcutaneous tunnel.

22. The method of claim 21 in which step d. comprises inserting the indwelling catheter into the hollow catheter prior to step c., the making of the subcutaneous tunnel with the hollow catheter thereby also moving the indwelling catheter from the second incision to and through the first incision.

23. The method of claim 22 in which step e. is performed prior to step f.

* * * * *